United States Patent [19]

Burgin

[11] Patent Number: 4,638,792
[45] Date of Patent: Jan. 27, 1987

[54] ADJUSTABLE SPECULUM WITH INCORPORATED LIGHTING SYSTEM

[76] Inventor: Kermit H. Burgin, R.R. #1, Box 334, Whitestown, Ind. 46075

[21] Appl. No.: 708,159

[22] Filed: Mar. 4, 1985

Related U.S. Application Data

[63] Continuation of Ser. No. 394,291, Jul. 1, 1982, Pat. No. 4,502,468, which is a continuation-in-part of Ser. No. 105,509, Dec. 20, 1979, Pat. No. 4,344,419, and a continuation-in-part of Ser. No. 354,812, Mar. 4, 1982, and a continuation-in-part of Ser. No. 284,484, Jul. 17, 1981, abandoned.

[51] Int. Cl.[4] ............................................... A61B 1/06
[52] U.S. Cl. ........................................... 128/6; 128/18
[58] Field of Search .................................. 128/15–18, 128/6, 9, 13, 14, 19

[56] References Cited

U.S. PATENT DOCUMENTS

| 605,652 | 6/1898 | Pitt . | |
|---|---|---|---|
| 765,887 | 7/1904 | Geyerman | 128/9 |
| 1,094,575 | 4/1914 | Joutras . | |
| 2,023,945 | 12/1935 | Allyn . | |
| 2,244,568 | 6/1941 | Palmeter . | |
| 2,292,237 | 2/1942 | Parcher | 128/9 |
| 2,544,932 | 3/1951 | Marco . | |
| 2,648,329 | 8/1953 | Mörch . | |
| 2,690,745 | 10/1954 | Govan . | |
| 3,324,850 | 6/1967 | Gunning et al. . | |
| 3,532,088 | 10/1970 | Fiore | 128/18 |
| 3,638,644 | 2/1972 | Reick . | |
| 3,716,047 | 2/1973 | Moore et al. . | |
| 3,762,400 | 10/1973 | McDonald . | |
| 3,890,961 | 6/1975 | Moore et al. . | |
| 3,916,881 | 11/1975 | Heine . | |
| 4,037,588 | 7/1977 | Heckele . | |
| 4,314,551 | 2/1982 | Kadell . | |
| 4,320,745 | 3/1982 | Bhitiyakul et al. . | |
| 4,323,304 | 4/1982 | Ishii | 128/6 |

FOREIGN PATENT DOCUMENTS

| 2302614 | 7/1974 | Fed. Rep. of Germany . | |
|---|---|---|---|
| 2801696 | 7/1979 | Fed. Rep. of Germany . | |
| 602084 | 6/1976 | Switzerland . | |
| 25040 | of 1913 | United Kingdom | 128/18 |
| 553728 | 6/1943 | United Kingdom | 128/18 |
| 612116 | 11/1945 | United Kingdom . | |

Primary Examiner—C. Fred Rosenbaum
Assistant Examiner—Gene B. Kartchner
Attorney, Agent, or Firm—Barnes & Thornburg

[57] ABSTRACT

A speculum includes a combination handle unit and a unitarily formed speculum head. The speculum head includes a portion for engaging a suitably configured handle unit and light-transmissive restraining or contacting members for dilating an orifice and conducting light from a source into the orifice to be examined. The handle unit includes a light source and a head portion suitably configured to accept the engaging portion of the speculum head.

4 Claims, 7 Drawing Figures

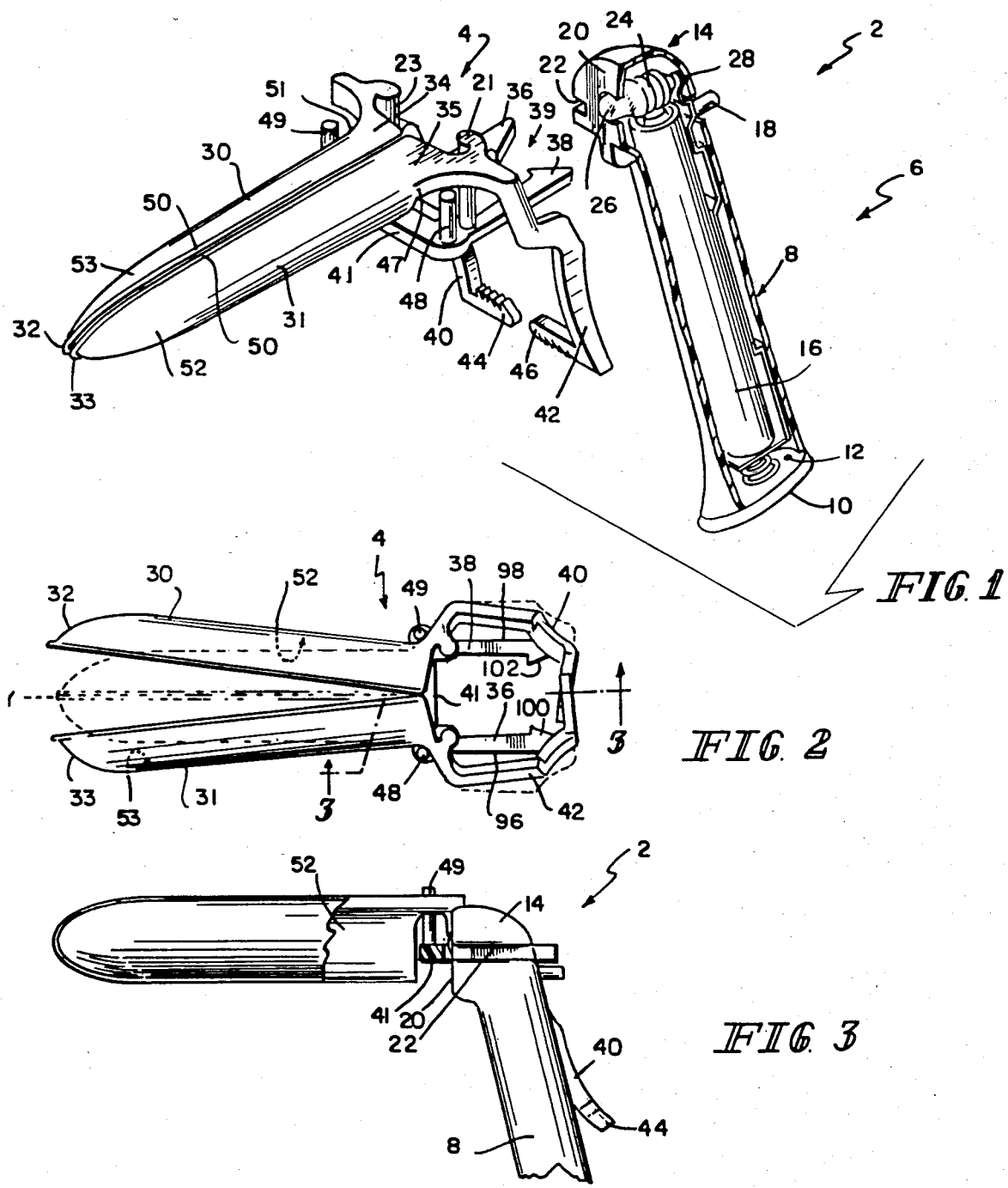

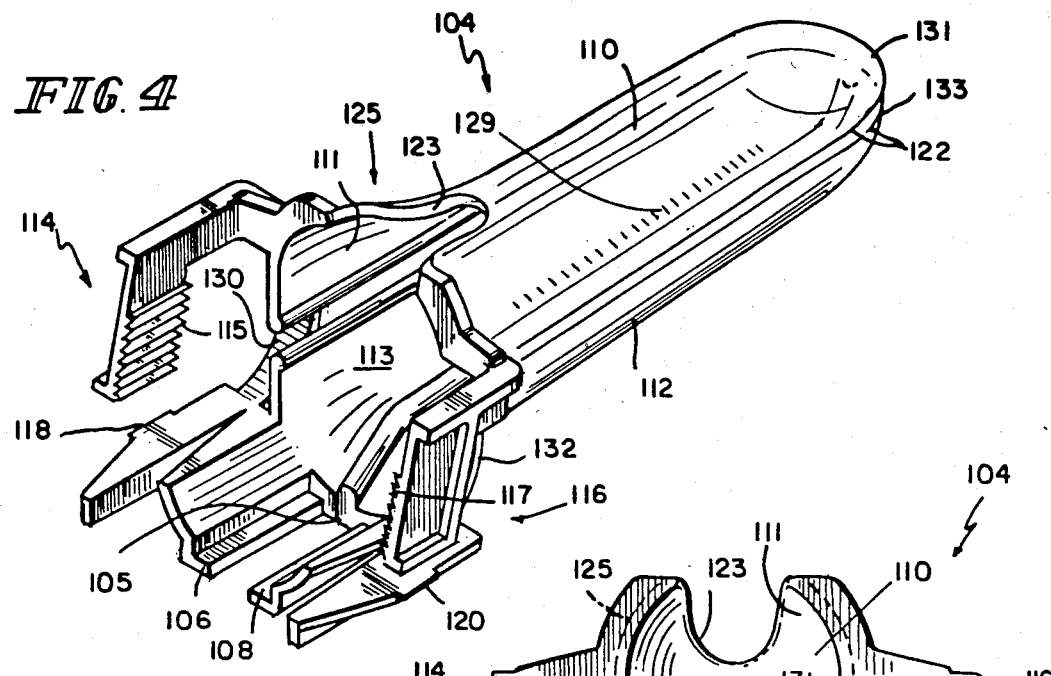
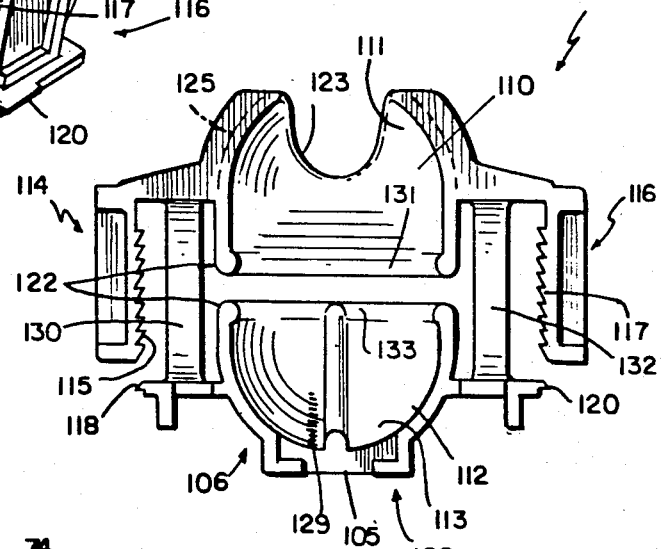
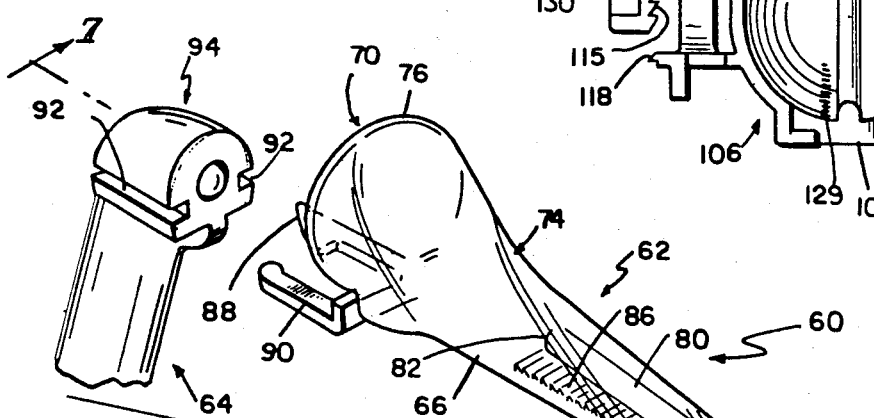
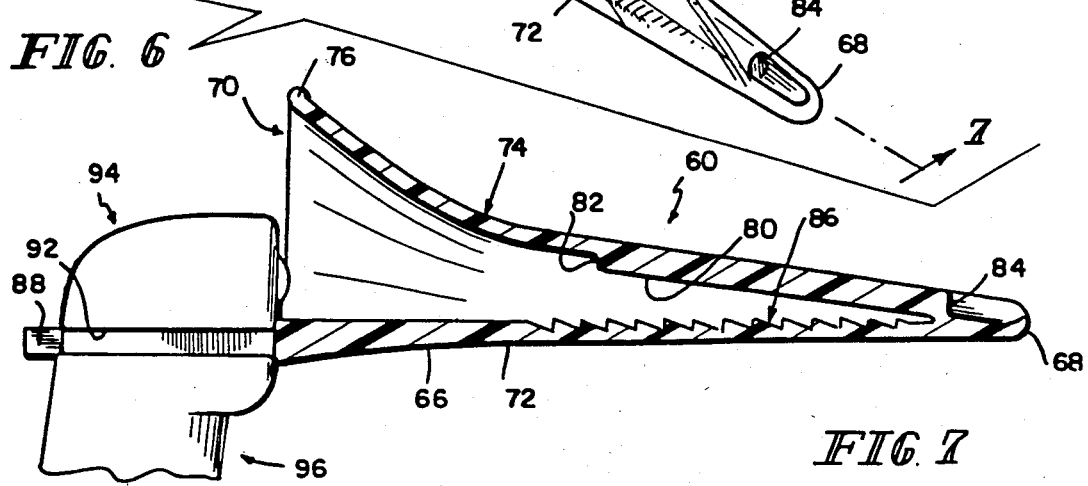

ADJUSTABLE SPECULUM WITH INCORPORATED LIGHTING SYSTEM

This is a continuation of application Ser. No. 394,291, filed July 1, 1982, now U.S. Pat. No. 4,502,468, which is a continuation-in-part of my co-pending U.S. patent application Ser. No. 105,509, filed Dec. 20, 1979 now U.S. Pat. No. 4,344,419; and a continuation-in-part of my now U.S. patent application Ser. No. 354,812, filed Mar. 4, 1982; and a continuation-in-part of my U.S. patent application Ser. No. 284,484, filed July 17, 1981, now abandoned.

The present invention relates generally to an apparatus for dilating a meatus, orifice, or incision. Certain embodiments disclose specula which provide means for independently adjusting the proximal and distal ends of the restraining members and wherein the restraining members are constructed from a light-transmissive material. The members are used to dilate the meatus, orifice, or incision. The members provide a means for sustaining various desired distances between the distal end thereof and a means for coupling the members to a combination handle and light source.

There are many well-known specula and forceps for enlarging body orifices or incisions for such purposes as examination or surgery. Many of these well-known devices require sterilization between uses; utilize independent light sources to illuminate the dilated meatus, orifice, or incision; or have means for adjustment situated such that the view and/or the ability of the user to examine the incision or orifice is at least partially obstructed. There are, for example, the devices described in the following documents: Molesworth U.S. Pat. No. 400,589; Crockett U.S. Pat. No. 776,302; Joutras U.S. Pat. No. 1,094,575; Radcliff U.S. Pat. No. 2,217,968; Batista U.S. Pat. No. 3,853,120; Marco U.S. Pat. No. 2,544,932; Moore et al U.S. Pat. No. 3,716,047; Moore et al U.S. Pat. No. 3,890,961; Smith U.S. Pat. No. 1,706,500; Rose U.S. Pat. No. 3,196,865; Crossley U.S. Pat. No. 1,230,873; Scheaff U.S. Pat. No. 1,222,478; Pitt U.S. Pat. No. 605,652; Gentile French Patent Specification No. 473,451; see also SURGERY, GYNECOLOGY AND OBSTETRICS, Vol. 68, No. 6, January 1939, pp. 1060–63; Fogarty et al U.S. Pat. No. 3,503,398; Galiano U.S. Pat. No. 399,749; Barnadet French Patent Specification No. 641,915; Raffaele Italian Patent Specification No. 246,611; and Pomerene U.S. Pat. No. 1,170,324.

Additionally, there are a number of medical examination instruments that utilize fiber optic or other light transmission techniques to illuminate a body orifice, meatus, or incision, such as the devices illustrated in U.S. Pat. Nos. 3,664,330; 3,762,400; 3,796,214; 3,716,047; 3,890,961; 2,247,258; 4,086,919; 3,851,642; 3,592,199; 3,324,850; 3,131,690; 2,482,971; and 3,978,850.

In accordance with the present invention, a speculum includes a base unit having a handle portion and a head portion, and a speculum head. The speculum head is provided with two blade-like contacting members, a support means, and means for resiliently supporting the contacting members on the support means. Attachment means are provided for removably securing the speculum head to the head portion of the base unit.

Illustratively, the base unit includes a light source for providing light in the head portion of the base unit.

In illustrative embodiments, the speculum head is constructed from a resilient material. The resilient material, in the area forming the blade-like contacting members, is light-transmissive.

Further according to illustrative embodiments, the contacting member support means comprises retainers on the proximal ends of the contacting members and having means for adjusting incrementally the distance between the distal portions of the contacting members. Further according to one illustrative embodiment, means are provided for limiting the maximum distance between the distal portions of the contacting members. Illustratively, the incremental adjustment means comprises two toothed portions selectively and incrementally engageable with each other. Alternatively, the two toothed portions may be selectively and incrementally engageable, each with its own pawl to adjust the contacting members' positions independently of one another.

In accordance with the present invention, an adjustable speculum is provided which is adaptable for use in enlarging and holding open orifices, incisions, and the like of various sizes, shapes, and depths. The speculum permits the user substantially unobstructed access to the orifice for examination and various other functions.

According to the invention, a speculum includes a speculum head having a portion for attachment to a handle, members for restraining and dilating an orifice, each member having a distal end for contacting the walls of the orifice and a proximal end hinged to the handle-attachment portion and means for adjusting and locking the distance between the distal ends of the restraining members.

Further, the present invention provides a speculum having a detachable dilating member which may be of various sizes or shapes and which may be sterilized or disposed of after each use.

Additionally according to the invention, the detachable dilating members are constructed from a light-transmissive material, such as an acrylic-styrene mixture, for use with a combination handle and light source unit. The detachable dilating members are constructed so that light from the source is directed through the light-transmissive material, and the handle and light source unit is constructed to engage the handle-attachment portions of the detachable dilating members frictionally.

Another embodiment in accordance with the invention is a speculum including an examination member for restraining and dilating an orifice, the member having a distal end for contacting the walls of the orifice and a proximal end rigidly attached to a handle-attachment portion.

Further, this last-mentioned embodiment in accordance with the invention provides a speculum having a detachable dilating member which may be of various sizes and shapes and may be sterilized or disposed of after each use.

Additionally, the detachable dilating member of this embodiment is constructed from a light-transmissive material such as an acrylic-styrene mixture, for use with a combination handle and light source unit. The detachable dilating member is constructed so that light from the source is directed through the light-transmissive material, and the handle and light source unit is constructed to engage the handle-attachment portions of the detachable dilating member frictionally.

The invention may best be understood from the following detailed description of certain embodiments thereof. In the description, reference is made to the accompanying drawings which illustrates the invention. In such drawings:

FIG. 1 is an exploded and partly fragmentary perspective view of an apparatus constructed in accordance with the present invention;

FIG. 2 is a top plan view of a portion of the apparatus of FIG. 1;

FIG. 3 is a sectional view of the apparatus of FIG. 1, but assembled, taken generally along section lines 3—3 thereof;

FIG. 4 is a perspective view of another apparatus constructed in accordance with the present invention;

FIG. 5 is an end view of the apparatus of FIG. 4, looking generally along section lines 5—5 of FIG. 4;

FIG. 6 is an exploded and partly fragmentary perspective view of another apparatus constructed according to the present invention; and FIG. 7 is a fragmentary sectional view of the apparatus of FIG. 6, assembled, taken generally along section lines 7—7 thereof.

Referring particularly to FIGS. 1-3, a speculum 2 includes a speculum head 4 and a base 6 which can be grasped by a physician to manipulate the speculum head. The base 6 has a somewhat pistol grip-shaped handle 8, a bottom cap 10 held on by screws 12, and a head portion 14. The handle 8 serves to hold one or more batteries 16 which provide a power source. If an alkaline battery is used, the battery can be molded into handle 8. Such a handle 8 may have a shelf life of up to five years and a useful life of up to six months. A switch 18 controls delivery of power from the batteries. Head 14 is provided with a forward face 20 and a groove 22 which extends longitudinally along both sides of head 14. Head 14 provides a socket 24 which receives an electric light bulb 26. Conductors 28, which illustratively are molded into the plastic material from which head 14 is formed, supply power through switch 18 from the batteries 16 to bulb 26.

As may be seen from FIG. 1, the speculum head 4 is molded in one piece from a moderately flexible, resilient plastic material which is also highly light-transmissive. Certain acrylic-styrene mixtures are suitable. Head 4 has a pair of blade-like contacting members 30, 31, each having a distal end 32, 33 for contacting and retaining a wall of an orifice, and a proximal end 34, 35. The speculum head 4 also has a support portion 41 for supporting the blade-like contacting members and means 39 for attaching the speculum head 4 to the head portion 14 of the base unit 6. The means 39 for attaching the speculum head 4 to the head portion 14 of the base unit includes two prongs 36, 38 provided on the support portion 41 of the speculum head 4 which frictionally engage in the groove 22 in the head portion 14 of the base unit 6.

The support portion 41 of the speculum head also includes two retaining members 40, 42. In this embodiment, the retaining members are somewhat L-shaped and have serrated or toothed lower portions 44, 46 that are incrementally and cooperatively engageable with each other. The two retaining members 40, 42 are attached to torsion means 21, 23 which are formed unitarily with the retaining members 40, 42 and the blade-like contacting members 30, 31. The torsion means 21, 23 are formed from a material that is sufficiently resilient to permit it to be adjusted several times without fatiguing or deforming under the stress. When the two retaining members 40, 42 are engaged and adjusted incrementally, the distance between the distal ends 32, 33 of the blade-like contacting members 30, 31 is increased or decreased, dependent on whether the adjustment of the engagement of the retaining members 40, 42 is contractive or expansive. The physician operator makes discrete adjustments to the distance between the distal ends 32, 33 of the blade-like contacting members 30, 31, and thereby expands or contracts the orifice, meatus, or incision by manipulation of the retaining members 40, 42. The torsion means 21, 23 provide sufficient tension to permit a snug engagement of retaining members 40, 42 during such manipulations by the physician operator. The support portion 41 has two stops 48, 49 that are selectively engageable with stop-engaging portions 47, 51 of the blade-like contacting members 30, 31 to provide a maximum adjustment of the retaining members 40, 42.

The outer edges 50 of the blade-like contacting members 30, 31 are beaded or rounded to remove any sharp edges from them and minimize the likelihood of tissue damage from edges 50. The blade-like contacting members 30, 31 preferably are constructed from some light-transmissive material, such as an acrylic-styrene blend. Light from light source 26, in the base 6, is directed down the concave inner surfaces 52, 53 of the blade-like contacting members 30, 31 and through the contacting members 30, 31 themselves directly into the orifice or incision.

Since the speculum head 4 is detachable from the base 6, various sizes and shapes of speculum heads 4 can be provided for the base 6, depending upon the size, shape, or depth of the orifice, incision, or meatus to be dilated. Furthermore, the blade-like contacting members 30 may have their distal ends 32 covered with a layer of some material (not shown) which is capable of absorbing body fluids.

FIG. 2 illustrates an adjusted orientation of the blade-like contacting members 30, 31 with respect to prongs 36, 38. When the retaining members 40, 42 are adjusted incrementally, the distal ends 32, 33 of the blade-like contacting members 30, 31 move equidistantly apart with respect to a line Y that is interjacent and parallel to the shaft-engaging prongs 36, 38. The mold joint of prongs 36, 38 to the support portion 41 is such that the outer surfaces 96, 98 of prongs 36, 38 are at right angles to the support means and parallel and planar with respect to each other. The prongs 36, 38 are provided with bevels 100, 102 to facilitate the frictional engagement between prongs 36, 38 and groove 22.

With reference to FIG. 3, the retaining members 40, 42 are formed such that the serrated or toothed lower portions 44, 46 are positioned behind the surface of handle 8 opposite the light socket 24 of head 14. The orientation of groove 22 with respect to the forward face 20 of head 14 is such that when the speculum head 4 is attached to handle 8, light from light source 28 is directed down the concave inner surfaces 52, 53 of the blade-like contacting members 30, 31.

FIG. 4 illustrates another one-piece speculum head 104 which can be used with handle 8 illustrated in FIG. 1. The head 104 has two prongs 106, 108 formed unitarily with a U-shaped support member 105 for engaging a head portion like portion 14 of FIG. 1. The two prongs 106, 108 are suitably configured to frictionally engage grooves 22 of handle 8. The speculum head 104 has two blade-like contacting members 110, 112 attached to the support member 105. The blade-like contacting member 110 includes two retaining members 114, 116. In the embodiment, the retaining members 114, 116 have serrated or toothed inner surfaces 115, 117 that are incrementally and cooperatively engageable with tabs 118, 120 formed on the outer surface of the U-shaped support member 105. The blade-like contacting members 110, 112 preferably are constructed from some light-transmissive material such as an acrylic-styrene blend. Light from any suitable light source, preferably the light source 28 illustrated in FIG. 1, is directed down the concave inner surfaces 111, 113 of the blade-like contacting members 110, 112 and through the blade-like contacting members 110, 112 themselves directly into the orifice or incision.

The two blade-like dilating members 110, 112 are hingedly attached to each other by hinge means 130, 132. The hinge means 130, 132 are unitarily formed with the blade-like dilating members 110, 112 and are resilient strips unitarily formed at one end to the retaining members 114, 116, and the other end is unitarily formed with the U-shaped support member 105. The hinge means 130, 132 are formed from a material that has sufficient resiliency to permit numerous operations of the speculum head 104 without deformation or breakage under the stress.

Edges 122 of the blade-like contacting members 110, 112 are beaded or rounded to remove any sharp edges from them and minimize the likelihood of tissue damages from edges 122. The upper blade-like contacting member 110 is formed such that an opening 123 is provided at its end 125 to enable an operator to insert surgical instruments or other devices into the dilated orifice. The lower blade-like contacting member 112 has measuring lines 129 molded along its length to facilitate making any measurements that may be desired.

Since the speculum head 104 is detachable from handle 8, various sized and shaped speculum heads 104 can be attached to the base 8, illustrated in FIG. 1, depending upon the size, shape, or depth of the orifice, incision, or meatus to be dilated. Furthermore, the blade-like contacting members 110, 112 may have their distal ends 131, 133 covered with a layer of some material capable of absorbing body fluids.

Referring now to FIG. 5, the retaining members 114 and 116 are substantially perpendicular to the U-shaped support member 105. As the serrated inner surfaces 115, 117 of the retaining members 114, 116 incrementally and cooperatively engage the tabs 118, 120 formed on the outer surface of the support member 105, the blade-like contacting member 110 distal end 131 moves away from the distal end 133 of the blade-like contacting member 112 in response to the engagement of the retaining members 114, 116 with the tabs 118, 120.

Referring now to FIGS. 6 and 7, a rectal speculum 60 includes a rectal examination head 62 and a base 64 which is substantially similar to base 6 illustrated in FIG. 1. The rectal examination head 62 has a hollow somewhat conical examination member 66 closed and rounded at its distal end 68 and flared and open at its proximal end 70. The examination head 62 also has a means for attaching the rectal examination head 62 to the base 64.

The entire surface 72 of the examination member 66, which is constructed at least partially from some light-transmissive material such as an acrylic-styrene blend, is smooth to minimize the likelihood of tissue damage from contact with the surface 72. The distal portion 68 of the examination member 66 is somewhat narrower in circumference than the proximal end 70 of the examination member 66. The increase in circumference from the distal end 68 to the proximal end 70 is achieved by a gradual flaring of the examination member 66. At point 74, the flare is increased to the proximal lip 76. In normal usage, the distal end 68 of the examination member 66 enters the rectum, then the remaining portion of the examination member 66 is inserted to fully dilate the orifice and thus permit as complete a field of view as possible for the operator. The discomfort and difficulty of dilating the orifice is minimized by having a gradual increase in circumference from the distal end 68 to the proximal end 70, thereby permitting a gradual dilation of the orifice as the examination member 66 is positioned.

The rectal examination head 62 has a light-guiding bar 80 that is substantially parallel to the longitudinal axis of the examination member 66. The light bar 80 has a light-receiving optical portion 82 and a light-emitting optical surface 84. The rectal examination head 62 also has a diffusion portion 86 adjacent to the light bar 80 and substantially perpendicular to the longitudinal axis of the examination member 66. In use, surface 84 is a major surface from which light rays transmitted through the light bar 80 exceed the critical angle. Thus, the majority of the light which enters the bar 80 exits through surface 84. The light emitted from the light-emitting optical surface 84 is somewhat directional rather than scattered and the light can be directed toward the field being examined. The diffusion portion 86 aids in diffracting any scattered rays directed back into the eyes of the operator.

The means for attaching the rectal examination head 62 to the base 64 includes two prongs 88, 90 unitarily formed with the proximal portion 70 of the examination member 66. Prongs 88, 90 frictionally engage in the groove 92 in the head portion 94 of the base 64.

What is claimed is:

1. An examination instrument, comprising
    a base unit having a somewhat pistol-grip shaped handle portion, and a head portion formed with said handle portion, said head portion comprising a first front surface and two side surfaces adjacent said front surface;
    a light source mounted in said head portion for providing light in said head portion of said base unit;
    a light-transmissive examination member for contacting a body surface to be examined;
    a means for removably attaching and securing said examination member to said head portion of said base unit such that said examination member is attached adjacent said light source, said attachment means including a groove extending at least partially across each of said two side surfaces, said grooves positioned on opposite sides of said head portion of said base unit and opening away from each other, said examination member including a proximal end portion configured with rearwardly projecting fingers spaced apart from each other along a rearward surface of said examination member a distance equal to the spacing of said grooves, said grooves receiving said fingers in sliding frictional engagement for sliding insertion of said examination member into, and sliding removal from said grooves.

2. The examination instrument of claim 1 wherein said head portion of said base unit further comprises a rear surface adjacent at least one of said two side surfaces and wherein at least one of said rearwardly projecting fingers includes a projection remote from its connection to said examination member for engaging said rear surface.

3. A speculum comprising
a base unit having a somewhat pistol-grip shaped handle portion and a head portion formed with said handle portion, said head portion comprising two opposed side surfaces,
a light source mounted in said base unit for providing light in said head portion of said base unit,
a light-transmissive speculum head for contacting a body surface to be examined, said speculum head having a support means, two blade-like contacting members for dilating an orifice, and a hinge means for hingedly connecting said two contacting members, said support means, said blade-like contacting members and said hinge means all being molded in a one-piece, flexible, resilient component, and
attachment means for removably securing said one-piece speculum head to said head portion of said base unit adjacent said light source said attachment means including a groove extending at least partially across each of said two opposed side surfaces, said grooves positioned on opposite sides of said head portion of said base unit, said speculum head including a proximal end portion configured with rearwardly projecting fingers spaced apart from each other along a rearward surface of said speculum head a distance equal to the spacing of the grooves, said grooves receiving said fingers in sliding frictional engagement for sliding insertion of said speculum head into, and sliding removal from, said grooves.

4. The speculum of claim 3 wherein said head portion of said base unit further comprises a rear surface adjacent at least one of said two opposed side surfaces and wherein at least one of said rearwardly projecting fingers includes a projection remote from said rearward surface of said speculum head for engaging said rear surface of said head portion of said base unit.

* * * * *